US007970456B2

(12) United States Patent
Preece et al.

(10) Patent No.: US 7,970,456 B2
(45) Date of Patent: Jun. 28, 2011

(54) METHOD AND APPARATUS FOR DETECTING THE PRESENCE OF DERMAL MELANIN IN EPITHELIAL TISSUE

(75) Inventors: Stephen John Preece, Cheshire (GB); Symon D'oyly Cotton, Cambs (GB); Robert James Morse, Cambridge (GB); Mark Chellingworth, Wales (GB)

(73) Assignee: Biocompatibles UK Limited, Surrey (GB)

( * ) Notice: Subject to any disclaimer, the term of this patent is extended or adjusted under 35 U.S.C. 154(b) by 1223 days.

(21) Appl. No.: 11/614,139

(22) Filed: Dec. 21, 2006

(65) Prior Publication Data
US 2007/0161910 A1 Jul. 12, 2007

(30) Foreign Application Priority Data
Dec. 23, 2005 (GB) .................................. 0526387.6

(51) Int. Cl.
A61B 6/00 (2006.01)
(52) U.S. Cl. ......... 600/473; 600/407; 600/475; 600/476
(58) Field of Classification Search .................. 600/407, 600/473, 475, 476, 478
See application file for complete search history.

(56) References Cited

U.S. PATENT DOCUMENTS

| | | | |
|---|---|---|---|
| 6,324,417 B1 | 11/2001 | Cotton | |
| 6,418,238 B1* | 7/2002 | Shiratani et al. | 382/133 |
| 6,433,767 B1 | 8/2002 | Murade | |
| 6,433,841 B1 | 8/2002 | Murade et al. | |
| 6,611,301 B2 | 8/2003 | Murade et al. | |
| 6,703,997 B2 | 3/2004 | Murade | |
| 6,762,809 B1 | 7/2004 | Murade | |
| 6,897,932 B2 | 5/2005 | Murade et al. | |
| 7,054,674 B2 | 5/2006 | Cane et al. | |

(Continued)

FOREIGN PATENT DOCUMENTS
GB 2 361 994 A 11/2001
(Continued)

OTHER PUBLICATIONS

Simon Cotton et al., "A Skin Imaging Method Based on a Colour Formation Model and its Application to the Diagnosis of Pigmented Skin Lesions," Proceedings of Medical Image Understanding and Analysis, 1999, pp. 49-52, Oxford.

(Continued)

Primary Examiner — Tse Chen
Assistant Examiner — John F Ramirez
(74) Attorney, Agent, or Firm — Oliff & Berridge, PLC

(57) ABSTRACT

An image of an individual (2) is obtained using a digital camera (1). The image data is then processed by ratio determination module (10) and an image conversion module (12) to analyze the image and determine data representative of the distribution of blood and melanin in the skin of the imaged individual. This chromophore distribution data is then processed by an image generation module (18) which generates an image representative of the expected appearance of epithelial tissue having the determined distribution of chromophores where the epithelial tissue is under fixed illumination and has a flat spatial geometry and where all the identified melanin is present solely in the epidermis. The presence of dermal melanin can then be identified by comparing the original image data and the image derived from processing the calculated chromophore distributions and identifying where the ratio of these images differs by more than a threshold, the threshold being set at a level above the amount of variation expected due to lighting and geometry differences.

19 Claims, 4 Drawing Sheets

U.S. PATENT DOCUMENTS

| | | |
|---|---|---|
| 7,132,943 B2 | 11/2006 | Nelson |
| 2001/0056237 A1* | 12/2001 | Cane et al. .................. 600/475 |
| 2003/0139672 A1 | 7/2003 | Cane et al. |
| 2005/0273011 A1 | 12/2005 | Hattery et al. |
| 2006/0089553 A1 | 4/2006 | Cotton |

FOREIGN PATENT DOCUMENTS

| | | |
|---|---|---|
| GB | 2 429 523 B | 3/2008 |
| JP | A 11-218781 | 8/1999 |
| JP | A 2001-166311 | 6/2001 |
| JP | A 2001-166312 | 6/2001 |
| JP | A 2003-262881 | 9/2003 |
| WO | 98/22023 | 5/1998 |
| WO | 00/75637 | 12/2000 |
| WO | 2004/010862 | 2/2004 |

OTHER PUBLICATIONS

European Patent Office, European Search Report for European Application No. 06256455.4, published May 14, 2008, pp. 1-3.

* cited by examiner

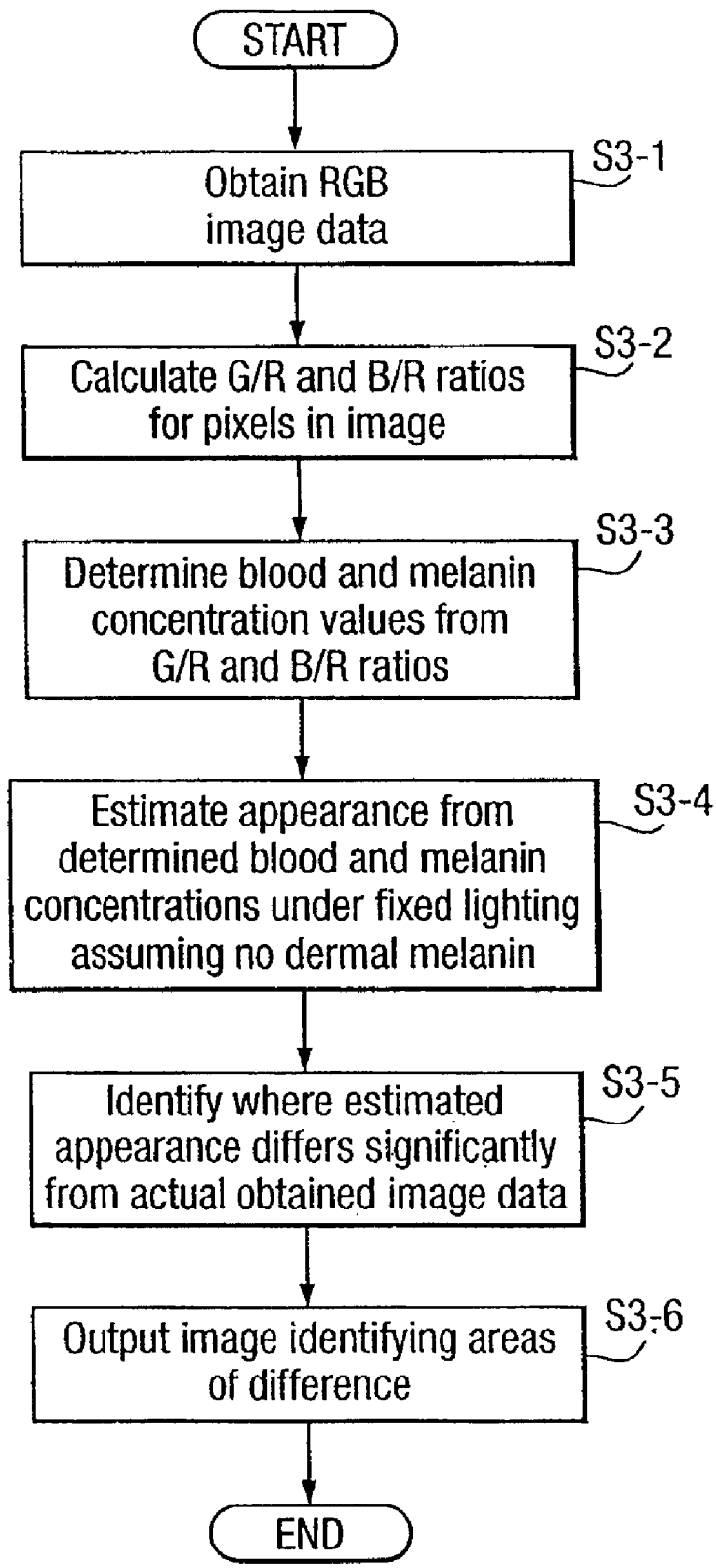

METHOD AND APPARATUS FOR DETECTING THE PRESENCE OF DERMAL MELANIN IN EPITHELIAL TISSUE

CROSS-REFERENCE TO RELATED APPLICATION

This application claims priority of U.K. Application No. 0526387.6, filed Dec. 23, 2005, which is hereby incorporated by reference in its entirety.

FIELD OF THE INVENTION

The present application concerns methods and apparatus for analysing epithelial tissue such as skin. In particular the present application concerns methods and apparatus for detecting the presence of dermal melanin in epithelial tissue.

BACKGROUND OF THE INVENTION

Over the last four decades there has been a world-wide increase in the incidence of melanoma. Although adequate sun protection has been identified as the first step toward preventing the occurrence of melanoma, early diagnosis and excision is the key to the survival of the many individuals who will still develop the disease.

A range of techniques have been developed to assess pigmented lesions. With the most common of these, dermatoscopy, a hand held microscope is used to visualise morphological characteristics at the dermo-epidermal junction. Clinicians then attempt to diagnose the presence of melanoma by analysing the lesion by colour, pattern and specific morphological features.

In addition to conventional dermatoscopy, a number of new techniques recently been developed by Astron Clinica Limited based on research undertaken at the University of Birmingham. These techniques are described in WO 00/75637 and WO 98/22023. The techniques use a quantitative understanding of the way light is absorbed and scattered within skin to produce maps of melanin, blood and collagen.

The original research undertaken at the University of Birmingham argued that the Kubelka-Munk theory is sufficient to model light transport within skin. If exact scattering and absorption coefficients can be specified, then the Kubelka-Munk theory can be applied at each wavelength in the visible range and corresponding remittance spectrum obtained. This predicted spectrum, which will determine the colour of the skin, will be dependent on the histological characteristics of the tissue. Three parameters capture most of the variation in remitted spectra from healthy skin. These three parameters are concentration of epidermal melanin, concentration of blood and thickness of the papillary dermal layer (collagen thickness).

Using the RGB response curves for a digital camera together with a model of the scattering and absorption characteristics of the skin, it is possible to calculate the set of image values which would be measured by a digital camera when skin with a known remittance spectrum $S(\lambda)$ is illuminated with light of known spectral characteristics $I(\lambda)$. This is done by calculating the convolution integral for each channel, given as, $$i_{red} = \int I(\lambda)S(\lambda)R(\lambda)d\lambda, \; i_{green} = \int I(\lambda)S(\lambda)G(\lambda)d\lambda, \; i_{blue} = \int I(\lambda)S(\lambda)B(\lambda)d\lambda$$

where $R(\lambda)$, $G(\lambda)$ and $B(\lambda)$ are the response curves for the red, green and blue channels and $i_{red}$, $i_{blue}$ and $i_{green}$ are the corresponding values recorded by the camera at a given pixel By ranging through all potential combination of melanin, blood and collagen, it is possible to generate all possible spectra and therefore all possible sets of image values which would be measured by a digital camera. Once this information has been obtained a link can be established between image values and histological parameter values. This link can be expressed as a mathematical function.

An image, acquired using a digital camera, consists of a large number of very small pixels, each of which have a set of image values, ($i_{red}$, $i_{green}$ and $i_{blue}$). By applying the mathematical function, linking these image values to histological parameter values, it is possible to obtain values for melanin, blood and collagen at every pixel within an image of skin. This information can then be displayed in the form of histological parametric map. The SIAscope®, developed by Astron Clinica Limited, relies on a specially adapted camera which is able to capture 4 channels of image data. As well the normal RGB channels, it also acquires an image in the infrared region of the spectrum. With this additional information, it is possible to produce an additional parametric map of dermal melanin.

Determining measurements of epidermal melanin, blood, collagen and dermal melanin directly from measurements of remitted light $S(\lambda)$ requires that a suspect lesion is illuminated with light of known spectral characteristics $I(\lambda)$. Using such an approach it is therefore necessary to follow a strict calibration procedure where lighting levels are strictly controlled. This limits the use of such an approach to analyzing small areas of skin as once larger areas of tissue are imaged, over which the surface geometry of the imaged tissue varies, calibration is no longer possible and analysis becomes inaccurate. The maps produced by such a technique have been shown to be of great value to clinicians in their diagnosis of melanoma. However, due to the required calibration procedures, it is typically only possible to produce a map of dermal melanin over a small area of skin, currently 15 mm diameter.

Although effective, prior art techniques thus currently require detailed individual analysis of every suspect lesion on a given patient and thus rely on the clinician being able to quickly identify all potentially dangerous lesions. While this is straight-forward for the majority of patients, some individuals present with large numbers of skin lesions. In this situation it would be useful to have some tool which would be able to automatically identify all lesions requiring a detailed inspection.

In order to overcome the problems arising due to strict calibration requirements an alternative technique has been developed. This is described in detail in Astron Clinica's prior patent application WO 04/010862. The technique relies on a mathematical function linking histological parameters with ratios of image values, rather than the actual image values. Determining measurements from ratios of image values removes the need for calibration. This can be demonstrated mathematically by considering the case where illumination which can be described by $$I(\lambda) = \alpha_1 \bar{I}(\lambda),$$

where $\alpha_1$ is a wavelength independent scaling factor which captures changes in illumination intensity and $\bar{I}(\lambda)$ captures the wavelength dependence of the incident light. The amount of light remitted from a tissue will depend on both the histological characteristics of the tissue and the angle of the tissue to the camera. The remitted spectrum can therefore be expressed as $$S(\lambda) = \alpha_2 \bar{S}(\lambda)$$

where $\alpha_2$ is a wavelength independent scale factor which depends on the angle of the tissue to the camera and $\overline{S}(\lambda)$ is the remitted spectrum which depends on the histology of the imaged tissue. Ratios of image values are now given as, $$r_{greenOverRed} = \frac{\alpha \int \overline{I}(\lambda)S(\lambda)G(\lambda)d\lambda}{\alpha \int \overline{I}(\lambda)S(\lambda)R(\lambda)d\lambda},$$

$$r_{blueOverRed} = \frac{\alpha \int \overline{I}(\lambda)S(\lambda)B(\lambda)d\lambda}{\alpha \int \overline{I}(\lambda)S(\lambda)R(\lambda)d\lambda}.$$

where $\alpha = \alpha_1 \alpha_2$. The factor $\alpha$, which captures all variation due to illumination changes and changes in surface geometry of the images tissue, will cancel out in each of the equations above leaving only wavelength dependent terms. Thus the image ratios can be seen to be independent of both illumination and surface geometry.

Variation in skin histology can then be thought of in terms of a parameter space and spectra are computed, using the Kubelka-Munk model, which correspond to each point with parameter space. By applying the above equations it is then possible to calculate the two image ratios $r_{greenOverRed}$ and $r_{blueOverRed}$ which correspond to a given spectra. Using the above technique, measurements of blood and melanin concentrations can be made without having to control for surface geometry and lighting conditions.

Although very effective for characterising normal skin, the described technique in WO 04/010862 is however limited to obtaining measurements of melanin and blood concentrations. The technique is not suitable for obtaining measurements of collagen as changes in collagen have an equal effect at every wavelength and therefore no effect on a ratio of two spectral measures. Further disclosed techniques are unable to determine whether melanin is present only within the epidermis of the skin or whether melanin has penetrated into the dermis. To be of use as a screening tool it must be possible to measure dermal melanin as if information showing the presence of dermal melanin could be displayed this would alert the clinician to any suspicious lesions An alternative system which assists with the identification of suspect lesions is therefore desirable.

SUMMARY OF THE INVENTION

In accordance with one aspect of the present invention there is provided an apparatus for detecting the presence of melanin in the dermis of an epithelial tissue having a dermis and an epidermis, said apparatus comprising:

a camera operable to obtain image data representative of light remitted by an epithelial tissue having a dermis and an epidermis illuminated by polarised light;

a chromophore determination module operable to process image data obtained by said camera to determine a measurement of the concentration of blood and melanin at points in an epithelial tissue in an obtained image; and a dermal melanin detection module operable to utilise measurements of the concentration of blood and melanin determined by said chromophore distribution module and image data obtained by said camera to determine the difference between detected remitted light from points in an epithelial tissue in an obtained image and expected levels of remitted light from epithelial tissue having said identified concentrations of blood and melanin in which said melanin is solely present in the epidermis of said epithelial tissue to identify points in said epithelial tissue where melanin is present in the dermis of said epithelial tissue.

In accordance with another aspect of the present invention there is provided a method of detecting the presence of melanin in the dermis of an epithelial tissue having a dermis and an epidermis, comprising:

obtaining image data representative of light remitted by an epithelial tissue having a dermis and an epidermis illuminated by polarised light;

processing obtained image data to determine a measurement of the concentration of blood and melanin at points in an epithelial tissue in an obtained image; and utilising said determined measurements of the concentration of blood and melanin and said obtained image data to determine the difference between detected remitted light from points in an epithelial tissue in an obtained image and expected levels of remitted light from epithelial tissue having said identified concentrations of blood and melanin in which said melanin is solely present in the epidermis of said epithelial tissue to identify points in said epithelial tissue where melanin is present in the dermis of said epithelial tissue.

BRIEF DESCRIPTION OF THE DRAWINGS

Further aspects and embodiments of the present invention will become apparent with reference to the accompanying drawings in which:

FIG. 3 is a flow diagram of the processing performed by the dermal melanin detection system of FIG. 1;

DETAILED DESCRIPTION OF THE INVENTION

Figure 1:
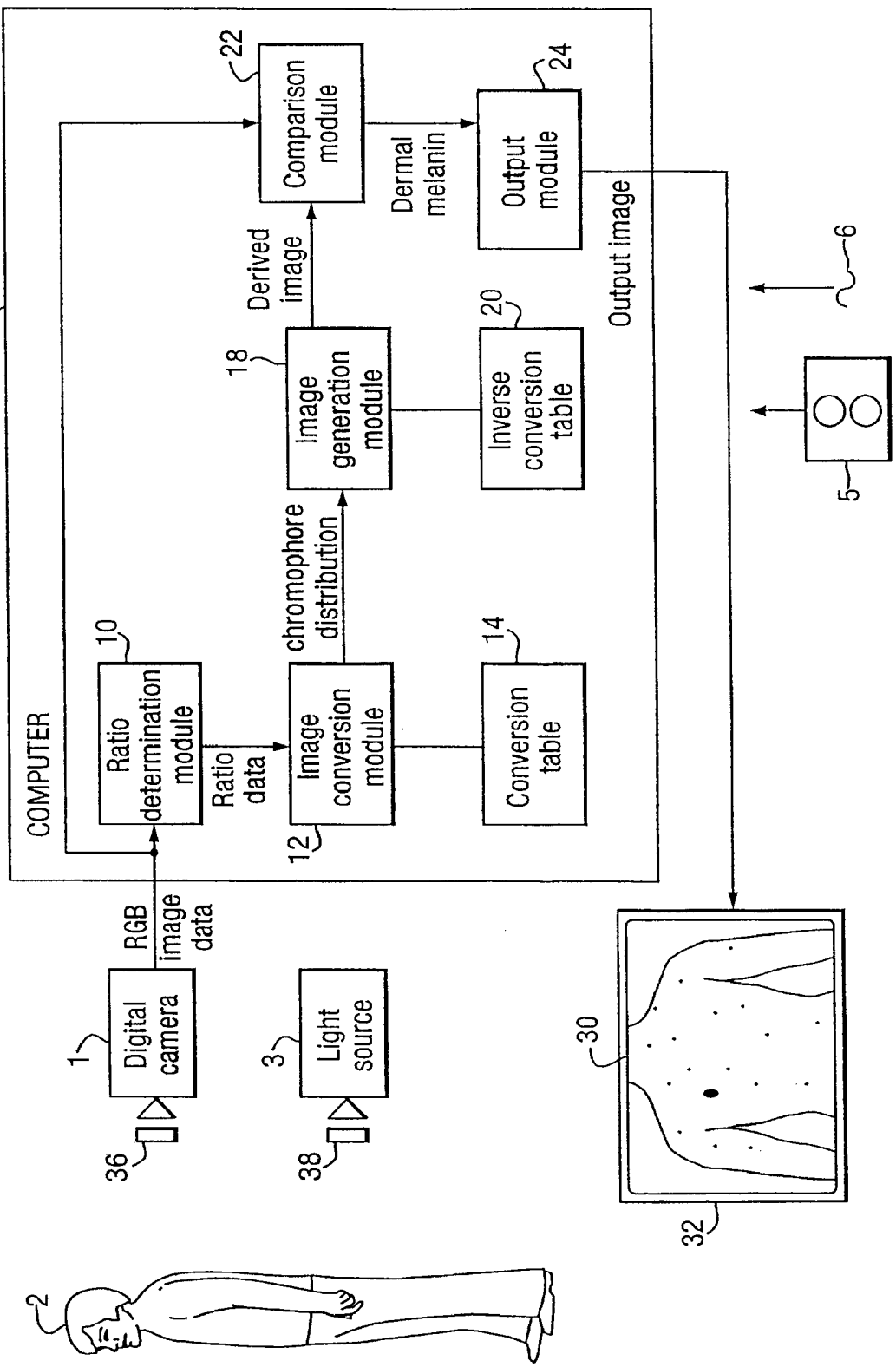
FIG. 1 is a schematic block diagram of a dermal melanin detection system in accordance with a first embodiment of the present invention.

FIG. 1 is a schematic block diagram of an embodiment of the present invention. In accordance with this embodiment, a digital camera 1 comprising a conventional digital camera is provided which is arranged to obtain an image of an individual 2 illuminated by a light source 3. The images obtained by the digital camera 1 are then transmitted to a computer 4 which is configured by software either provided on a disk 5 or by receiving an electrical signal 6 by via a communications network to be configured into a number of functional modules 10-24 which cause the computer 4 to process the image data received from the digital camera 1 to generate an output image 30 which is shown on a display 32.

In the present embodiment the functional modules 10-24 comprise: a ratio determination module 10 for converting RGB image data into ratio data, an image conversion module 12 and a conversion table 14 for processing ratio data to generate data indicative of concentrations of blood and melanin; an image generation module 18 and an inverse conversion table 20 operable to generate derived image data utilizing chromophores distribution data; a comparison module 22 for comparing received RGB image data and derived image data generated by the image generation module 22; and a output module 24 for outputting an output image on basis of the comparison between received and derived image data performed by the comparison module 22.

The functional modules 10-24 illustrated in FIG. 1 are purely notional in order to assist with the understanding of the working of the claimed invention and may not in certain embodiments directly correspond with blocks of code in the source code for the software. In other embodiments the function performed by the illustrated functional modules 10-24 may be divided between different modules or may be performed by the re use of the same modules for different functions.

As will be described in detail later, the processing undertaken by the ratio determination module 10 and the image conversion module 12 is similar to that described in Astron Clinica's prior patent application WO 04/010862. This enables the computer to process image data obtained by the digital camera 1 and determine measurements of blood and melanin present in the skin of the individual 2 being analysed. The image generation module 18 and inverse conversion table 20 are then utilised to process the determined measurements to generate image data representative of the expected appearance of skin including such chromophore concentrations, where all of the identified melanin is assumed to be present in the epidermis. The comparison of this derived image with the actual image data from the digital camera 1 by the comparison module 22 then enables areas where melanin is present in the dermis of the individual's skin to be identified. As is explained this identification is achieved without having to control the lighting illuminating the individual 2 being analysed and hence enables the imaging an analysis of large areas of an individual's skin in a single image.

The accuracy of the system of the present embodiment has been compared with the detection of dermal melanin using conventional techniques. In tests involving data collected from 25 lesions 9 melanomas and 16 benign lesions, assessment of all lesions showed a perfect match between identification of dermal melanin utilising the above described system and conventional techniques for all the melanomas. For the benign lesions all results agreed apart from one which showed a low presence of dermal melanin using conventional techniques where none was identified using the above technique.

Interaction of Light with the Skin

Prior to describing the detailed processing of the various functional modules 10-24 of the computer 4, the physical structure of skin and the interaction of skin with light will be briefly explained with reference to FIG. 2.

Figure 2:
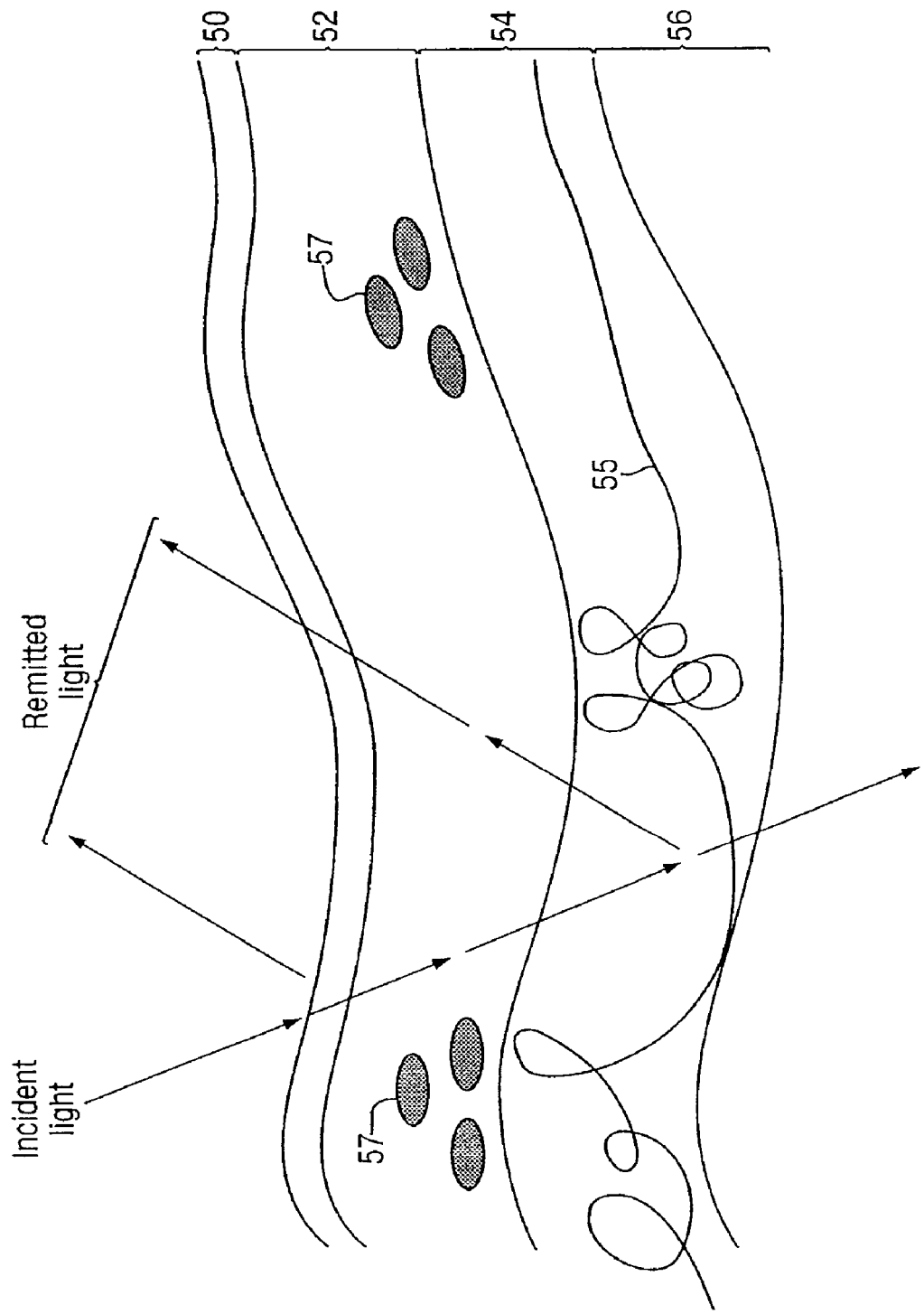
FIG. 2 is a schematic cross sectional view through a layer of skin illustrating the structure of the skin and the interaction of that structure with incident light.

As shown in FIG. 2, skin has a layered structure comprising an outer cornified layer 50, the epidermis 52, and the dermis which itself can be divided into the papillary dermis 54 which contains the blood supply 55 for the skin and the reticular dermis 56.

When light is incident on the skin, much of the light is immediately reflected when coming into contact with the outer cornified layer 50. A proportion of incident light does, however, pass through the cornified layer 50 and proceeds to interact with the constituents of the epidermis 52 and the papillary dermis 54.

As light passes through the epidermis 52 and the papillary dermis 54 the light is absorbed by various chromophores present in the skin, most notably chromophores such as hemoglobin present in the blood in blood vessels 55 in the papillary dermis, melanin, a pigment produced by melanocytes 57 in the epidermis 52 and collagen a fibrous material present throughout the skin. By the time the incident light reaches the reticular dermis 56 the scattering of light is highly forward and therefore for that reason the reticular dermis 56 can for all intents and purposes be considered returning no light.

In addition to chromophores present in the epidermis 52 and papillary dermis 54 absorbing various wavelengths, certain structures in the skin most notably collagen cause incident light to be reflected. The outward appearance of the skin can therefore be considered to be a mixture of the light immediately reflected by the cornified layer 50 and the remitted light which has interacted with the chromophores present in the epidermis 52 and the papillary dermis 54. As has been demonstrated in the applicant's prior U.S. Pat. No. 6,324,417 and co-pending U.S. patent application Ser. Nos. 09/760,387, 10/240,071, 10/521,639 and 10/532,158 all of which are hereby incorporated by reference it is possible to process light remitted from the skin to obtain measurements of various chromophores present in the skin.

In order to obtain measurements of the concentrations and distribution of chromophores in the papillary dermis 54 and epidermis 52, the effect of reflection of light directly by the cornified layer 50 is required to be removed so that a measurement of the remitted light which has interacted with the chromophores present in the epidermis 52 and papillary dermis 54 can be made.

Returning to FIG. 1, in this embodiment a first polarising filter 36 is provided in front of the lens of the digital camera 1 and a second polarising filter 38 cross polarised with the first is provided in front of the light source 3. As the interaction of light with collagen in the skin is such to cause the light to lose its polarisation, by providing these filters. Light from the light source 3 passing through the second polarising filter 38 which is reflected directly by the cornified layer 50 without interacting with the other layers of the skin is caused to be filtered by the first polarising filter 36. The image data obtained by the digital camera 1 is thereby caused to be solely representative of the light remitted which has interacted with the structures of the epidermis 52 and papillary dermis 54 of an individual's skin.

Processing of Obtained Image Data

Referring to FIG. 3 which is a flow diagram of the processing performed by the computer 4 of FIG. 1, initially (S3-1) an image is obtained by the digital camera 1 of the individual 2 illuminated by the light source 3. In this embodiment the digital camera 1 comprises a conventional digital camera. The image data generated by the digital camera 1 therefore comprises RGB values ranging from 0 to 255 for a large array of pixels where the RGB values are indicative of the extent light received by a photo receptor within the camera 1 for each pixel in an image appears to be red, green and blue where a completely black pixel has RGB values of 0, 0, 0 and a completely bright white pixel has RGB values of 255, 255, 255.

When an image of an individual 2 has been obtained by the camera 1, the image is then passed to the ratio determination module 10 which converts (S3-2) the conventional RGB data for each pixel in an image into ratio data. This is achieved by the ratio determination module processing the received RGB image data and determining for each pixel in a received image the ratio of the value for the green channel for a pixel relative to the value for the red channel for that pixel and the ratio of the value for the blue channel for the pixel relative to the value for the red channel for the pixel. By processing the image data for each pixel in a received image in this way a pair of ratio values $r_{greenOverRed}$ and $r_{blueOverRed}$ is derived for each of the pixels. Ratio data comprising an array of the determined ratio values is then passed by the ratio determination module 10 to the image conversion module 12.

After the ratio determination module 10 has converted the RGB values for an image into ratio data, the image conversion module 12 then processes (s3-3) the generated array of ratio values to obtain values indicative of the concentration of blood and melanin at individual points on the surface of the skin of the individual.

In this embodiment this is achieved by processing each pair of ratio values for each pixel $r_{greenOverRed}$ and $r_{blueOverRed}$ in an array in turn by scaling the ratio values so the scaled ratio values comprise integer values ranging 0 and 1023. These scaled ratio values are then utilised to access the conversion table 14 which in this embodiment is a 1024 by 1024 a lookup table associating pairs of scaled ratio co-ordinates with pairs of concentrations of blood and melanin liable to give rise to such ratio values. In this embodiment, the conversion table 14 comprises a table associating blood and melanin concentrations with various ratio values, where the ratio values fall within and slightly beyond the expected range of the colour space for skin. In the event that the combination of $r_{geenOverRed}$ and $r_{blueOverRed}$ values for a particular pixel falls outside the range of values for which chromophores concentration data is stored within the conversion table 14, in this embodiment the conversion module 12 returns a null value for the concentration of blood and melanin for the pixel with such $r_{greenOverRed}$ and $r_{blueOverRed}$ values.

After chromophore distribution values for blood and melanin for each of the pixels in an image have been calculated by the conversion module 12, this chromophore distribution data is then passed by the conversion module 12 to the image generation module 18 which together with the inverse conversion table 20 proceeds to determine (S3-4) derived image data representative of the appearance of skin having containing the determined distribution of blood and melanin concentrations as determined by the image conversion module 12 under fixed lighting conditions where all the melanin in the skin is present only in the epidermis 52.

In this embodiment, this conversion is achieved by the image generation module 18 accessing the inverse conversion table 20 which is a lookup table which associates each possible pair of determined blood and melanin concentrations for a pixel with a set of expected RGB values, where the expected RGB values are derived from a model of the interaction of skin with light. In the case of pixels which are associated with values of within the chromophore distribution data no RGB values are determined. This derived image data is then passed to the comparison module 22 which proceeds (s3-5) to utilize the differences between this derived image data and the actual image data obtained by the digital camera 1 to identify portions of an image corresponding to concentrations of dermal melanin.

Figure 4A:
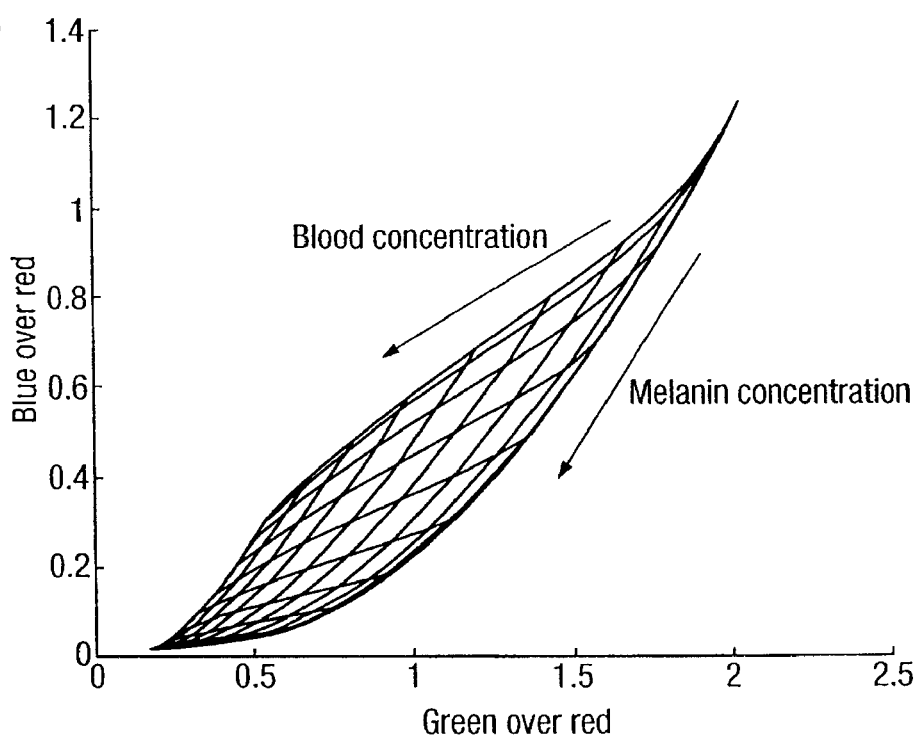
FIG. 4A is a plot of ratios of green/red and blue/red remitted light for a sample of epithelial tissue illustrating the effect of increasing epidermal melanin and blood in the absence of dermal melanin.

To appreciate the processing undertaken by the comparison module 22 to derive information relating to dermal melanin, it is first necessary to understand the effect of introducing dermal melanin on the ratios of the image values. FIG. 4A shows a plot of the ratios $r_{greenOverRed}$ against $r_{blueOverRed}$ for varying concentrations of epidermal melanin and blood. Each vertex of the grid represents a different combination of epidermal melanin and blood, with the arrows showing how the ratios change as each of the parameters is increased. It can be seen that as either epidermal melanin or blood concentration increases, both ratios decrease.

Figure 4B:
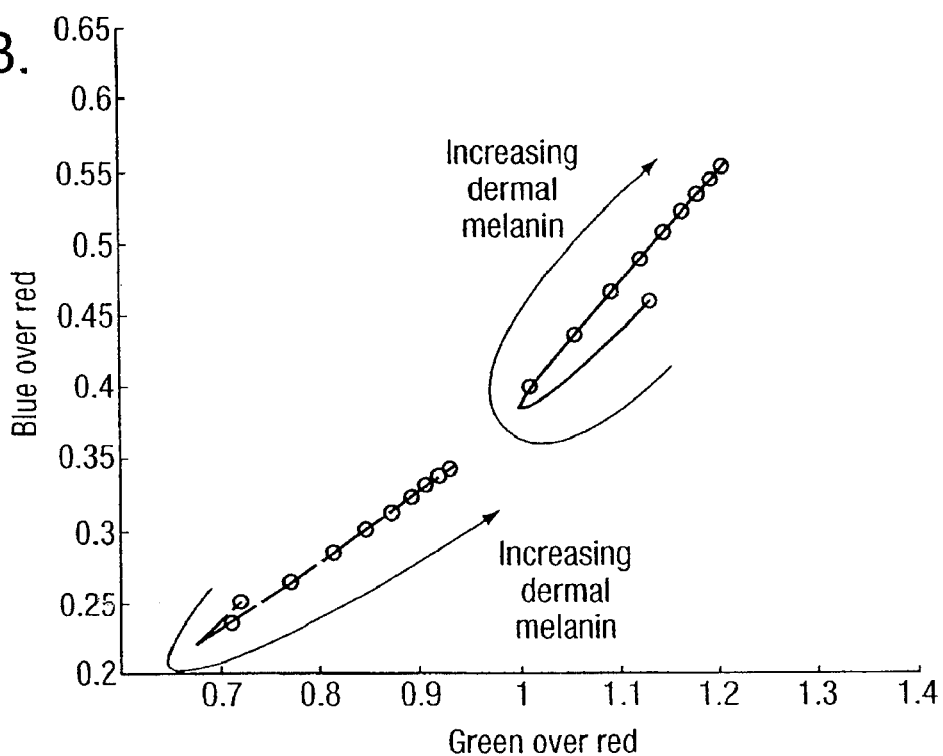
FIG. 4B is a plot of ratios of green/red and blue/red remitted light for a sample of epithelial tissue illustrating the effect of increasing dermal melanin concentration for two separate combinations of epidermal melanin and blood concentrations.

FIG. 4B shows a plot of $r_{greenOverRed}$ against $r_{blueOverRed}$ for varying dermal melanin concentration for two fixed combinations of epidermal melanin and blood. It can be seen that increasing dermal melanin has a different effect on the ratios to increasing epidermal melanin. For the two curves the ratios $r_{greenOverRed}$ and $r_{blueOverRed}$ are seen to decrease initially followed by a rapid increase as dermal melanin concentration increases. Ten circles have been shown on the curves at equally incremented values of dermal melanin concentration and illustrate how the behaviour changes from a decrease to an increase. It can be seen that, after a very small increase in dermal melanin concentration the trajectory of the ratios rapidly changes.

This change arising due to variations in concentration in dermal melanin has been verified experimentally through comparing light remitted by normal skin and skin known to contain dermal melanin. Analysing remitted light from a normal mole where the epidermal melanin concentration is known to increase as predicted by the theory both the ratios $r_{greenOverRed}$ and $r_{blueOverRed}$ can be observed to decrease. In contrast analysing remitted light from a blue naevus, which is a skin lesion known to have increasing dermal melanin concentrations, the ratios are observed to increase initially and then to decrease as is predicted by the model.

In this embodiment, when the comparison module 22 receives derived image data from the image generation module 18, initially the comparison module 22 determines a ratio $\alpha(x,y)$ for the red channel value for each pixel in a derived image relative to the actual value for the red channel for each corresponding pixel in the image obtained by the camera 1.

If the illumination and surface geometry of the imaged tissue are identical at every point then $\alpha(x,y)$ will have same value at every point. As illumination or surface geometry of the tissue varies there is a corresponding change in the values of $\alpha(x,y)$. Additionally, as well as capturing changes in illumination and tissue geometry, $\alpha(x,y)$ also gives a good indication of how far points deviate from the model of normal skin illustrated in FIG. 4A. Ratios of image values, obtained from an image of normal skin, will decrease as epidermal melanin increases as demonstrated earlier. In contrast dermal melanin causes an increase in image ratios. Increasing image values correspond to less epidermal melanin and therefore lighter skin.

Thus if $\alpha(x,y)$ is calculated at a point $(x,y)$ where there is a high concentration of dermal melanin it will be much lower than the surrounding tissue. This is because high dermal melanin concentration will result in high image ratios and therefore a low prediction of epidermal melanin. Low epidermal melanin will give rise to a large predicted value for $i_{red}$ but the actual value will be low due to the presence of dermal melanin. This will then produce a low value for $\alpha(x,y)$.

In practice, although variations in $\alpha(x,y)$ for pixels in an image also capture variation in illumination intensity and changes in surface geometry, these factors only result in a change in $\alpha(x,y)$ of about 20-30%. In contrast variations in dermal melanin concentration typically result in a change in $\alpha$ of about 3-4 times.

Image data identifying portions of an image corresponding to concentrations of dermal melanin can therefore be determined by applying a suitable thresholding function to the $\alpha$ values. In this embodiment, this is achieved by the comparison module 22 using the following function:

$$\alpha_{map}(x, y) = \frac{\alpha_{bg}}{\alpha(x, y)} - 1.5$$

where $\alpha_{bg}$ is the mean value of $\alpha$ across normal skin, $\alpha(x,y)$ is the ratio derived for pixel $(x,y)$ and where all negative value of $\alpha_{map}$ are set to zero. In this embodiment, the value $\alpha_{bg}$ for an image is derived by thresholding the original image to find areas which are significantly darker than the surrounding skin and then determining the average α value determined for portions of the image excluding those areas darker than a threshold. These dark areas are excluded as they would normal constitute areas of abnormally high melanin concentration, such as within a mole.

The above function results in a normalised quantity which increases dramatically as the value of α(x,y) decreases. By subtracting the factor 1.5, variations due to illumination change and tissue geometry are effectively removed leaving only variation due to the presence of dermal melanin.

After values of $\alpha_{map}(x,y)$ have been derived for all pixels for which blood and melanin concentrations were derived by the image conversion module 12, this measure indicative of the presence of dermal melanin is passed to the output module 24. The output module 24 then causes the calculated $\alpha_{map}(x,y)$, which typically range between 0 and 4 to be scaled so as to range between 0 and 255 and then (s3-6) causes an image 30 representing the calculated $\alpha_{map}(x,y)$ values to be displayed on the screen of the display 32.

Although in the above embodiment, a specific method for obtaining measurements of blood and melanin concentrations based on ratios of RGB colour values has been described, it will be appreciated that the above system could be adapted to utilise measurements of blood and melanin concentrations obtained by different means.

Thus for example instead of obtaining image data for red, green and blue colour channels, image data representative of other colour channels could be utilised. In such alternative embodiments ratio data could be calculated using data from any channel captured using a digital camera, where a channel is defined to be some linear combination of wavelengths in the UV, visible or IR regions of the electromagnetic spectrum, having an intensity can be measured using an appropriately designed optical filter.

Although in the above embodiment ratio data is described as being obtained by dividing image data of other colour channels by image data for a red colour channels, it will be appreciated that other ratios could be utilised. In general, however, it is preferable that ratio data is obtained by dividing image data for a high frequency colour channel by image data for a lower colour channel. This is because data obtained for lower frequency colour channels tends to be more stable and hence reduces the variability in the obtained ratios.

In other alternative embodiments, processing image data to obtain ratio data could be replaced by a conversion of RGB image data into appropriate polar co-ordinates. In such embodiments, colour angles defining an apparent hue could be utilised in a similar way to the described ratio data to obtain estimated measurements of blood and melanin concentrations.

In the above embodiment, a ratio α(x,y) for the red channel value for each pixel in a derived image relative to the actual value for the red channel for each corresponding pixel in the image obtained by the camera 1 is determined which is a measure of the illumination and surface geometry of imaged tissue. In alternative embodiments, a measurement of the actual 3D geometry of the tissue being imaged could be obtained and the image data representative of the expected appearance of imaged tissue having the measured geometry could then be generated. By providing a system in which the actual geometry of an imaged tissue was measured, expected variations in appearance due to surface geometry could then be modelled. Areas of difference between the actual appearance of tissue and the appearance of tissue modelled assuming that melanin is present only in the dermis could then be identified.

Although in the above embodiment, the difference between the derived image and actual image is characterised using a method of based on a ratio calculation, this differences could also be parameterised with some other mathematical formula, for example, some form of normalised difference.

Although the embodiment of the invention described with reference to the drawings comprises computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means.

When a program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

It is to be understood that the exemplary embodiments are merely illustrative of the invention and that many variations of the above-described embodiments may be devised by one skilled in the art without departing from the scope of the invention. It is therefore intended that all such variations be included within the scope of the following claims and their equivalents.

What is claimed is:

1. A method of detecting the presence of melanin in the dermis of an epithelial tissue having a dermis and an epidermis, the method comprising:
   obtaining an image of epithelial tissue to be analysed;
   processing said obtained image to determine from said image, data representative of a distribution of blood and melanin within said tissue;
   utilising said determined distribution of blood and melanin and a model of the propagation of light through epithelial tissue to generate image data representative of the expected appearance of epithelial tissue containing said determined distribution of blood and melanin wherein said determined distribution of melanin is assumed to be contained solely within the epidermis of said epithelial tissue; and
   detecting the presence of dermal melanin by identifying portions of said generated image which differ from corresponding portions of said obtained image by an amount greater than an amount due to expected variations in appearance due to variations in illumination and surface geometry, wherein detecting the presence of dermal melanin comprises:
   determining for portions of said image the ratio of image data for at least one colour channel of image data in said generated image relative to the ratio of the image data for said at least one colour channel of image data in said obtained image;

determining an average ratio value for the image data for said at least one colour channel of image data in said generated image relative to the image data for said at least one colour channel of image data in said obtained image; and identifying portions of said image where said ratio of image data for said at least one colour channel of image data in said generated image relative to the image data for said at least one colour channel of image data in said obtained image exceeds said average value by a threshold.

2. The method in accordance with claim 1 wherein said threshold comprises a threshold in excess of the expected variation of said ratio data arising due to variations in illumination of said epithelial tissue and surface geometry of said epithelial tissue.

3. The method in accordance with claim 1 wherein said threshold is such that identifying portions of said image where said ratio of image data for said at least one colour channel of image data in said generated image relative to the image data for said at least one colour channel of image data in said obtained image exceeds said average value by a threshold comprises identifying portions of said image where said ratio exceeds said average ratio by more than 30%.

4. The method in accordance with claim 1, wherein determining an average ratio value for image data comprises:
identifying portions of an obtained image representative of epithelial tissue having low concentrations of melanin;
determining an average ratio value for the image data for said at least one colour channel of image data for said identified portions of said generated image relative to the image data for said at least one colour channel of image data in said portions of said obtained image.

5. The method in accordance with claim 1 wherein said colour channel comprises a colour channel comprising longer wavelengths of visible light.

6. The method in accordance with claim 1 wherein said colour channel comprises a red or infra-red colour channel.

7. A method of detecting the presence of melanin in the dermis of an epithelial tissue having a dermis and an epidermis, the method comprising:
obtaining an image of epithelial tissue to be analysed;
processing said obtained image to determine from said image, data representative of a distribution of blood and melanin within said tissue;
utilising said determined distribution of blood and melanin and a model of the propagation of light through epithelial tissue to generate image data representative of the expected appearance of epithelial tissue containing said determined distribution of blood and melanin wherein said determined distribution of melanin is assumed to be contained solely within the epidermis of said epithelial tissue; and
detecting the presence of dernial melanin by identifying portions of said generated image which differ from corresponding portions of said obtained image by an amount greater than an amount due to expected variations in appearance due to variations in illumination and surface geometry, wherein said processing said obtained image to determine from said image data representative of a distribution of blood and melanin within said tissue comprises:
storing model data defining a relationship between concentrations of blood and melanin and data indicative of the apparent colour of epithelial tissue including said concentrations of blood and melanin; and
processing an obtained an image of epithelial tissue to be analysed utilising said stored model data to determine the distribution of blood and melanin in the epithelial tissue being analysed.

8. The method in accordance with claim 7 wherein said model data comprises data defining a relationship between concentrations of blood and melanin and data indicative of the expected ratios of image data in three different colour channels of image data of epithelial tissue including said concentrations of blood and melanin wherein processing said obtained image further comprises:
processing obtained image data to determine for portions of said obtained image ratio data indicative of the ratio of image data of different colour channels for said portions of said obtained image; and
utilising said determined ratios and said stored model data to determine the concentrations of blood and melanin in portions of the epithelial tissue being analysed.

9. The method in accordance with claim 8 wherein said colour channels comprise: red, green and blue colour channels.

10. An apparatus for detecting the presence of melanin in the dermis of an epithelial tissue having a dermis and an epidermis, comprising:
a camera operable to obtain an image of epithelial tissue to be analysed;
a processing module operable to process images obtained by said camera to determine from said obtained images data representative of a distribution of blood and melanin within an imaged epithelial tissue;
an image generation module operable to utilise distributions of blood and melanin determined by said processing module to generate image data representative of the expected appearance of epithelial tissue containing said determined distribution of blood and melanin wherein said determined distribution of melanin is assumed to be contained solely within the epidermis of said epithelial tissue; and
a comparison module operable to detecting the presence of dermal melanin in an imaged epithelial tissue by identifying portions of an image generated by said image generation module for determined blood and melanin distributions for said imaged epithelial tissue which differ from corresponding portions of an obtained image of said epithelial tissue by an amount greater than an amount due to expected variations in appearance due to variations in illumination and surface geometry, wherein said comparison module comprises:
a ratio determination module operable to determine for portions of images obtained by said camera, the ratio of image data for at least one colour channel of image data in an image generated by said image generation module relative to the ratio of the image data for said at least one colour channel of image data in said obtained image;
an average calculation module operable to determine an average ration value for the image data for said at least one colour channel of image data in a generated image relative to the image data for said at least one colour channel of image data in an obtained image; and
an identification module operable to identify portions of said image where the ratio of image data for said at least one colour channel of image data in a generated image relative to the image data for said at least one colour channel of image data in an obtained image exceeds an average value by a threshold.

11. The apparatus in accordance with claim 10 wherein said identification module is arranged so that said threshold comprises a threshold in excess of the expected variation of said ratio data arising due to variations in illumination of said epithelial tissue and surface geometry of said epithelial tissue.

12. The apparatus in accordance with claim 10 wherein said identification module is arranged so that said threshold is such that identifying portions of said image where said ratio of image data for said at least one colour channel of image data in said generated image relative to the image data for said at least one colour channel of image data in said obtained image exceeds said average value by a threshold comprises identifying portions of said image where said ratio exceeds said average ratio by more than 30%.

13. The apparatus in accordance with claim 10, wherein said average calculation module is operable to:
  identify portions of an obtained image representative of epithelial tissue having low concentrations of melanin; and
  determine an average ratio value for image data for said at least one colour channel of image data for said identified portions of said generated image relative to the image data for said at least one colour channel of image data in said portions of said obtained image.

14. The apparatus in accordance with claim 10 wherein said colour channel comprises a colour channel comprising longer wavelengths of visible light.

15. The apparatus in accordance with claim 10 wherein said colour channel comprises a red or infra-red colour channel.

16. An apparatus for detecting the presence of melanin in the dermis of an epithelial tissue having a dermis and an epidermis, comprising:
  a camera operable to obtain an image of epithelial tissue to be analysed;
  a processing module operable to process images obtained by said camera to determine from said obtained images data representative of a distribution of blood and melanin within an imaged epithelial tissue;
  an image generation module operable to utilise distributions of blood and melanin determined by said processing module to generate image data representative of the expected appearance of epithelial tissue containing said determined distribution of blood and melanin wherein said determined distribution of melanin is assumed to be contained solely within the epidermis of said epithelial tissue;
  a comparison module operable to detecting the presence of dermal melanin in an imaged epithelial tissue by identifying portions of an image generated by said image generation module for determined blood and melanin distributions for said imaged epithelial tissue which differ from corresponding portions of an obtained image of said epithelial tissue by an amount greater than an amount due to expected variations in appearance due to variations in illumination and surface geometry; and
  a measuring unit operable to obtain measurements of the surface geometry of an epithelial tissue; wherein said image generation module operable to utilise distributions of blood and melanin determined by said processing module to generate image data representative of the expected appearance of epithelial tissue having a surface geometry corresponding to a surface geometry obtained by said measuring unit and containing said determined distribution of blood and melanin wherein said determined distribution of melanin is assumed to be contained solely within the epidermis of said epithelial tissue, wherein said processing module operable to determine data representative of a distribution of blood and melanin within an imaged epithelial tissue comprises:
  a model store operable to store model data defining a relationship between concentrations of blood and melanin and data indicative of the apparent colour of epithelial tissue including said concentrations of blood and melanin; and
  a determination module operable to process an obtained an image of epithelial tissue to be analysed utilising said stored model data to determined the distribution of blood and melanin in the epithelial tissue being analysed.

17. The apparatus in accordance with claim 16 wherein said model data comprises data defining a relationship between concentrations of blood and melanin and data indicative of the expected ratios of image data in three different colour channels of image data of epithelial tissue including said concentrations of blood and melanin wherein determination module comprises:
  a ratio calculation module operable to process obtained image data to determine for portions of said obtained image ratio data indicative of the ratio of image data of different colour channels for said portions of said obtained image, said determination module being operable to utilise ratios determined by said ratio calculation module and model data stored in said model store to determine the concentrations of blood and melanin in portions of the epithelial tissue being analysed.

18. The apparatus in accordance with claim 17 wherein camera is operable to obtain image data comprising image data for red, green and blue colour channels.

19. An apparatus for detecting the presence of melanin in the dermis of an epithelial tissue having a dermis and an epidermis, comprising:
  a camera operable to obtain an image of epithelial tissue to be analysed;
  a processing module operable to process images obtained by said camera to determine from said obtained images data representative of a distribution of blood and melanin within an imaged epithelial tissue;
  an image generation module operable to utilise distributions of blood and melanin determined by said processing module to generate image data representative of the expected appearance of epithelial tissue containing said determined distribution of blood and melanin wherein said determined distribution of melanin is assumed to be contained solely within the epidermis of said epithelial tissue;
  a comparison module operable to detecting the presence of dermal melanin in an imaged epithelial tissue by identifying portions of an image generated by said image generation module for determined blood and melanin distributions for said imaged epithelial tissue which differ from corresponding portions of an obtained image of said epithelial tissue by an amount greater than an amount due to expected variations in appearance due to variations in illumination and surface geometry;
  a measuring unit operable to obtain measurements of the surface geometry of an epithelial tissue; wherein said image generation module operable to utilise distributions of blood and melanin determined by said processing module to generate image data representative of the expected appearance of epithelial tissue having a surface geometry corresponding to a surface geometry obtained by said measuring unit and containing said determined distribution of blood and melanin wherein said determined distribution of melanin is assumed to be contained solely within the epidermis of said epithelial tissue;

a polarized light source operable to illuminate a sample of epithelial tissue to be analysed with polarized light; and a polarizing filter, wherein said polarizing filter is operable to filter out light having the same polarity of the polarized light said polarized light source is operable to illuminate a sample of epithelial tissue and wherein said camera is arranged to obtain an image of a sample of epithelial tissue illuminated by said polarized light source as viewed via said polarizing filter.

* * * * *